United States Patent [19]

Fortune et al.

[11] Patent Number: 4,919,322
[45] Date of Patent: Apr. 24, 1990

[54] DESOLDERING TIP AND REPLACEMENT APPARATUS

[76] Inventors: William S. Fortune, 29866 Cuthbert Rd., Malibu, Calif. 90265; Robert E. Dallons, 6625 Tamarind, Agoura, Calif. 91301

[21] Appl. No.: 320,085

[22] Filed: Mar. 6, 1989

[51] Int. Cl.$^5$ .............................................. B23K 3/00
[52] U.S. Cl. ........................................ 228/20; 228/57; 29/235; 29/283; 222/570; 239/266; 239/397
[58] Field of Search ................... 228/20, 57, 191, 264, 228/54; 29/157 C, 235, 267, 283; 222/570; 239/266, 397

[56] References Cited

U.S. PATENT DOCUMENTS

| | | | |
|---|---|---|---|
| 3,180,533 | 4/1965 | Sundholm | 222/570 |
| 3,549,078 | 12/1970 | Fortune | 228/20 HT |
| 3,612,409 | 10/1971 | Henning | 222/570 |
| 4,564,989 | 1/1986 | Sogandares | 29/235 |

Primary Examiner—Richard K. Seidel
Assistant Examiner—Samuel M. Heinrich
Attorney, Agent, or Firm—Daniel T. Anderson

[57] ABSTRACT

A hand held, spring actuated single stroke piston desoldering instrument having a removable, replaceable nozzle tip in combination with a novel removal tool which also serves as a holder for several spare tips is disclosed. The barrel of the desoldering instrument is one-piece molded and includes an end cap portion with a forwardly protruding nose portion having a nozzle retaining central bore therethrough. The novel replaceable nozzle element has two annular grooves formed about its periphery: the first mates with an annular reduced diameter shoulder within the retaining bore of the end cap; the second is normally disposed forwardly of an outside of the end cap where it may be gripped by a pair of flexible jaws on the removal tool. A pair of fins on th sides of the nose portion of the end cap engage a cam on the ends of the jaws in a manner such that upon squeezing the jaws together to grip the nozzle while axially rotating the desoldering tool with respect to the removal tool, the nozzle is forcefully pulled from the nose of the desoldering tool.

6 Claims, 3 Drawing Sheets

U.S. Patent   Apr. 24, 1990   Sheet 1 of 3   4,919,322
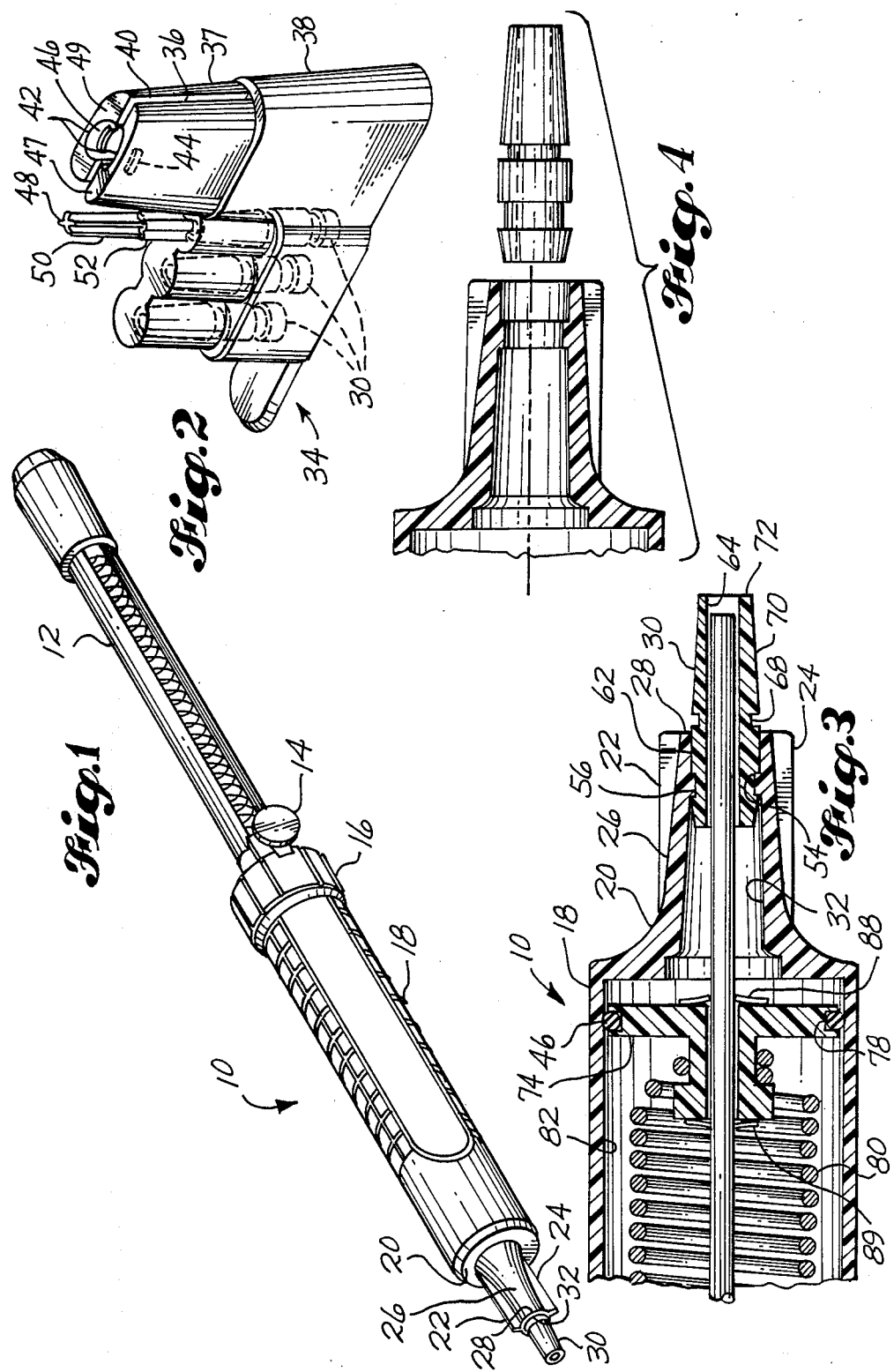

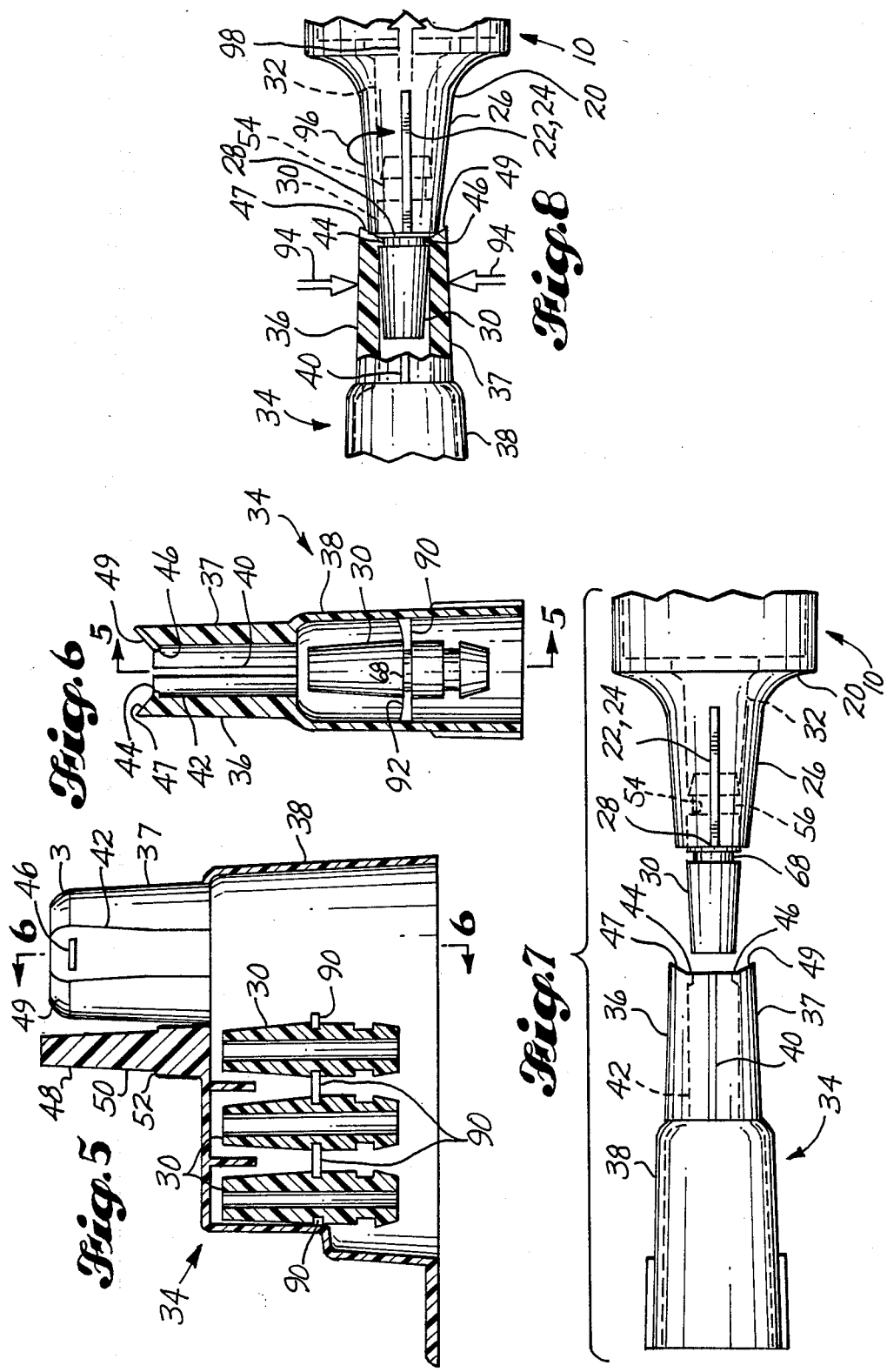

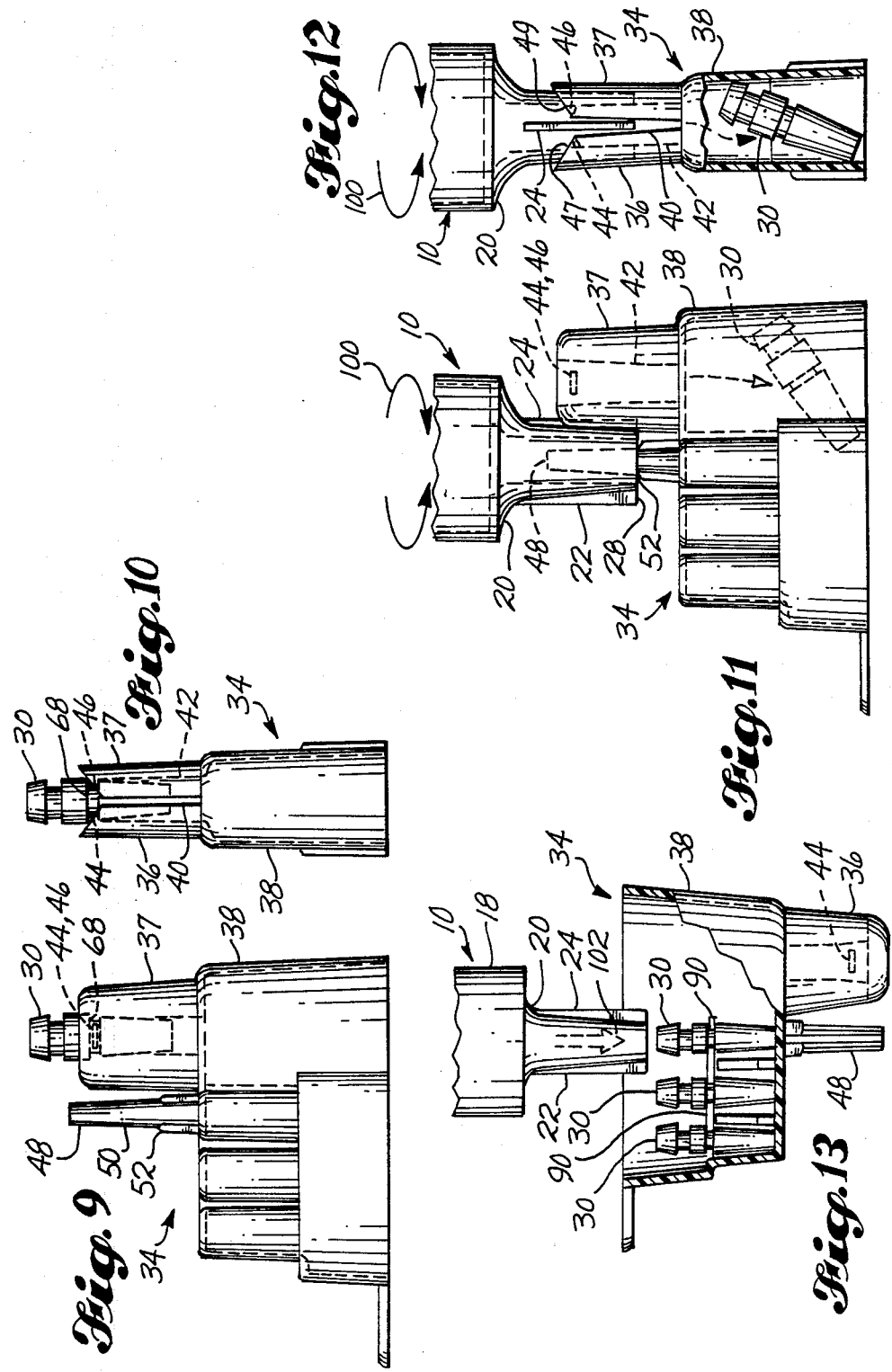

DESOLDERING TIP AND REPLACEMENT APPARATUS

BACKGROUND OF THE INVENTION

1. Field of the Invention

The invention relates generally to removing or lifting or drawing away, by air suction technique, small quantities of particulate, liquid, or molten matter and particularly to apparatus improvements in hand held, hand operated vacuum stroke cleaning devices. The present invention finds particularly useful application in the field of soldering, desoldering, and rewiring in electronic laboratories, maintenance shops, factories, or hobbyists' benches; and although, in the cause of clarity and brevity, much of the following discussion and description of examples of the invention are directed theretoward, it is expressly to be understood that the advantages of the invention are equally well manifest in other fields wherever and whenever substances are to be removed or cleaned from an object such, for further example, in medical or dental fields as in removal of foreign objects or unwanted substances from portions of the body including the eye, ear, nose, throat, or open wound or the like.

2. Background of the Invention

In the electrical arts as mentioned, it is often desired to desolder an electrical connection such as, for example, a wire wrapped terminal, a wire to circuit board terminal, the terminals of a surface mounted device such as an integrated circuit chip, or the like. The removal, from the connection, of the molten solder without dropping or spattering it onto other portions of the equipment is generally essential. Blowing or shaking the molten metal away is therefore not an acceptable practice; and, in combination with its high mass density, the high surface tension associated with the solder makes its removal particularly difficult. Furthermore, the problem is aggravated by the requirement that the solder be removed quickly and without application of cooling means before the mechanical connection such as a multi-terminal microcircuit chip-to-circuit board or a wire-wrapped terminal may be taken apart.

3. Description of Prior Art

Since 1963 the art of molten solder removal has been developed, in large measure by the present applicants, with the invention and extensive improvement of hand held, single stroke, spring driven piston desoldering tools having an air intake, or suction, nozzle at their front end for drawing in molten solder as the spring driven piston is triggered by the operator to fly back. The progression of such tools is exemplified by the following U.S. Pat. Nos. 3,114,026 issued Dec. 10, 1963, to William S. Fortune; 3,263,8889 issued Aug. 2, 1966, to William S. Fortune; 3,818,539 issued June 25, 1974, to William S. Fortune, and 4,765,229 issued Aug. 23, 1988, to William S. Fortune and Robert E. Dallons.

For a number of reasons these tools generally utilize a small, tubular plastic nozzle held removably by the front end of the body of the desoldering tool: the plastic is less likely to cause damage by impact upon delicate components; plastics such as Teflon are self lubricated such that molten solder and flux materials do not fuse with or otherwise stick to them; and such plastics are readily and inexpensively machine and supplied as replaceable, spare parts with choice of configuration with respect to nozzle length, inner diameter, and curvature. When such plastic materials are used, however, they are subject to wear and significant deterioration from the very hot and caustic environment in which the tip inherently operates. Accordingly, their replaceability is important economically. A particularly commercially significant such replaceable tip is shown and described in U.S. Pat. No. 4,204,299 issued May 27, 1980 to William S. Fortune.

Specific Disadvantages of the Prior Art

It has been difficult to provide a replaceable tip which is easy to remove and replace and yet maintain a tight air seal between the tip and the forward end of the desoldering tool. The problem is aggravated by the fact that the plastic materials are vulnerable to damage if grasped forcefully by normal tools such as gas pliers or vice jaws.

A further disadvantage of the prior art is that the replaceable tips are small and, being machined from material such as Teflon, are relatively expensive. Thus, if a supply of replacement tips of different geometries is to be kept in a handy location on the benchtop, the individual tips are subject to loss and are typically difficult to locate and select from when hurriedly needed.

Particular objects of the Invention

Accordingly, it is an object of the present invention to provide a replaceable such desoldering tip which is not subject to these and other disadvantages and limitations.

It is another object to provide a tip which is readily and easily replaceable and which is relatively easy and inexpensive to manufacture.

it is another object to provide such a tip which exhibits a good air seal between it and the front end of the desoldering tool.

It is another object to provide such a tip and a cooperating tool for very easily and quickly removing and replacing it.

It is another object to provide such a tool which in magazine fashion retains and organizes a predetermined selection of spare tips.

It is another object to provide a desoldering tool, tip replacing tool, and replacement tip which cooperatively achieve the above advantages.

SUMMARY OF THE INVENTION

Briefly these objects are achieved in the present invention by providing a desoldering tool having a molded plastic front end which includes a protruding end cap having one or more levering fins molded therewith and extending axially forwardly to the end thereof and formed with a nozzle receiving bore therethrough with a nozzle retaining annular shoulder therein for grasping a mating annular first groove about the periphery of a plastic tubular nozzle insert element of the combination. The nozzle element has a second annular groove disposed forwardly of the receiving bore which is of the character to be grasped by the tip replacing tool of the combination. The tool has a pair of flexible jaws having internal, opposing gripping tabs for grasping the tip element when the jaws are urged together by the fingers of the operator. The replacing tool also has a cam surface formed by the outward end of each of the jaws which engages the forward end of the levering fin of the desoldering tool, the cam surface being of the character to push the fin, and thereby the desoldering tool body, away from the tip when the two tools are relatively rotated about the longitudinal axis of the desoldering tool while pressing the gripping tabs of the jaws into the second annular groove of the nozzle.

The nozzle, or tip, is thusly removed from the desoldering tool and held in turn firmly by the jaws of the removing tool. To release the nozzle from the jaws, they are spread by placing the desoldering tool bore over a release peg disposed contiguously to the jaws. By so placing the tool over the release peg, the levering fin is driven between the jaws thereby spreading them and releasing the nozzle element.

The removal tool element has a magazine portion formed therewith for holding readily removably at least one spare nozzle by its outer second annular groove. Thusly the rear portion thereof may be directly inserted into an empty end cap bore of the desoldering tool where it is grasped by its inner first annular groove for proper installation in the forward end of the desoldering tool.

The combination and subcombinations of features which characterize and define the invention are set forth with particularity in the claims. The invention itself, however, both as to structural organization and operation, as well as additional objects and advantages thereof will best be understood from the following description read in connection with the drawing.

BRIEF DESCRIPTION OF THE DRAWING

FIG. 1 is a perspective view of a desoldering tip and replacement apparatus combination constructed in accordance with the principles of the invention;

FIG. 2 is a perspective view of the tip removal tool element thereof showing three spare tips retained therewithin;

FIG. 3 is a longitudinal sectional view of the front portion of the apparatus shown in FIG. 1;

FIG. 4 is a similar view illustrating the separation of the nozzle element therefrom;

FIG. 5 is a longitudinal sectional view of the apparatus shown in FIG. 2 and taken along the reference lines 5—5 of FIG. 6;

FIG. 6 is a crossectional view thereof taken along the reference lines 6—6;

FIG. 7 is an elevational view of the desoldering tool front end with a nozzle element therein and the tip removal tool;

FIG. 8 is similar view, partly in section, showing the removal tool in engagement with the nozzle element for effecting its removal;

FIG. 9 is a front elevation view of the removal tool element with a just removed nozzle element being held thereby;

FIG. 10 is an end elevation view thereof;

FIG. 11 is a front view thereof illustrating the release thereby of the nozzle element;

FIG. 12 is an end view thereof partly in section; and

FIG. 13 is front view partly in section of the removal tool showing its magazine of spare nozzles and indicating the method of inserting one thereof into the front end of the desoldering tool.

DESCRIPTION OF PREFERRED EMBODIMENT

Referring specifically to FIG. 1, the example shown of the desoldering tool component of the combination is a spring actuated desoldering implement 10 including a cocking plunger 12, a stroke actuating trigger 14, a trigger housing bushing 16, and a barrel 18 having, in this example, an end cap 20 molded integrally therewith. The end cap, in turn, is formed with a pair of levering fins 22, 24 extending axially along a nozzle retaining portion 26 to its forward end 28. A replaceable, machined Teflon tip or nozzle 30 is shown installed in the axially extending nozzle retaining bore 32 of the portion 26. The fundamental structure and operation of the desoldering implement 10 is similar in its essential aspects to that shown and discussed in the above enumerated prior art patents to which reference is made for any desired understanding of basic such desoldering implements and their operation or of desoldering techniques in general. The balance of this specification, in the cause of brevity and clarity, is directed toward the molded front end portion of the implement and its cooperation with the other elements of the combination claimed hereinafter.

In FIG. 2 the tip removal tool 34 is shown with its flexible jaws 36, 37 cantilevered upwardly from their attachment to the tool base 38 with which they, in this example, are integrally molded. It may be noted that the juxtaposed jaws are separated by a gap 40 and by nature of their flexible cantilevered configuration may be pushed either toward or further apart from each other. The jaws 36, 37 are internally relieved in opposing regions to form cooperatively a tip receiving bore 42 and each jaw is formed with an inwardly protruding nozzle gripping tab 44, 46. The top, end surfaces of the jaws each form an outwardly diverging cam 47, 49 which are described and explained below.

A release peg 48 is disposed in line with the gap 40 and protrudes upwardly from its connection to the base 38 with which it also may be integrally molded. The upper portion 50 of the peg has an outer cross dimension such that it slides closely but loosely into the tip retaining bore 32 of the desoldering implement end cap 20 when there is no nozzle installed therein. The implement 10 then may be fitted vertically over the peg 48 in axial alignment therewith until the front end of the end cap abuts the larger shoulder 52. When the end cap is thusly placed over the peg, for reasons discussed below, one of the levering fins 22, 24 is normally placed within the gap 40 whereby by twisting the body of the desoldering implement 10 about its longitudinal axis and with respect to the body of the removal tool 34, the levering fin forces one of the jaws 36, 37 away from the other thereby increasing the width of the gap 40 and further spreading apart the griping tabs 46, 44.

The bottom of the removal tool 34 is essentially open and is molded to form a magazine for retaining three spare tips 30 which are removable from below as discussed in connection with the description of FIG. 13.

Referring to FIGS. 3 and 4, the sectional views of the front portion of the desoldering implement 10 shows the barrel 18 molded integrally with the end cap 20 which in turn includes the levering fins 22, 24 and the tip retaining portion 26 with its forward end 28 and the tip retaining bore 32. In FIG. 3, the nozzle 30 is shown installed within the bore 32 while in the exploded view of FIG. 4, the nozzle 30 is shown separated axially from its retaining bore 32.

Axially inwardly from the end 28 of the end cap 20 a reduced diameter annular retaining shoulder 54 is disposed which is molded to mate with an annular first groove 56 machined about the circumference of the Teflon tip 30. Between the groove 56 and the rear end 58 of the tip, the outer diameter of the tip is reduced by tapering with a frustoconical surface 60 to slightly less than that of the retaining shoulder 54 to aid in inserting the tip 30 into its retained engagement with the bore 32.

The central portion 62 of the tip has an outer diameter approximately equal to that of the front portion 64 of the bore 32 has an outer diameter approximately equal to that of the front portion 64 of the bore 32 whereby when inserted the tip and the retaining bore 32 form a firm and substantially sealed connection so that the suction stroke of the implement 10 forces a maximum of air flow through the internal bore 66 of the nozzle 30.

Just forward of the central portion 62 of the tip 30 a second annular, outer groove 68 is provided about the circumference of the tip, and its character is such that the gripping tabs 44, 46 of the removal tool's jaws 36, 37 may be inserted therein for grasping the nozzle and, as described below, forcefully pulling it from the retaining bore 32 when its replacement is desired. The forward portion 70 of the tip 30 may be tapered to a reduced, minimum diameter at its forward end 72 for maximum accessibility to an intricate workpiece, maximum visibility to the workpiece by the operator, and minimum mass at the forward end of the hand held tool.

The remaining detail of FIG. 3 includes a sectional view of the vacuum producing piston 74 which carries a sealing o-ring 76 in a retaining groove 78 about its periphery whereby when the piston is drawn back in its vacuum stroke by the cocking spring 80, the o-ring provides a sliding seal with the inner cylinder wall 82 of the barrel 18. The piston 74 is formed with a retaining groove 84 for the reduced diameter forward end 86 of the spring 80 which in effect is wrapped snugly around it. The piston is held on a plunger, cocking shaft 86 by a pair of crimp washers 88, 89. The shaft 86 is held forwardly against the tension of the cocking spring 80 by the trigger 14 until released thereby to create the fly-back vacuum stroke. It may be noted that, in this example, the cocking shaft 86 extends forwardly well into the bore 64 of the tip 30 as a cleaning rod. Accordingly, with each cocking stroke the bore is cleaned of pieces of solder, flux, and like materials. In other examples, the forward cleaning rod extension of the shaft may be a separate rod carried by the piston and replaceable as by a threaded attachment with rods of other diameters to accommodate the effective cleaning of nozzles having different diameter inner bores 64.

Referring to FIGS. 5 and 6, the sectional views of the removal tool 34 illustrate in detail the construction of the molded article with the vertical cantilevered flexible jaws 36, 37 each having its nozzle gripping tab 44, 46 projecting into the tip receiving bore 42 formed in the juxtaposed faces of the jaws. Again the top end surfaces of the jaws are formed to provide cams 47, 49 which slope divergingly away from the gap 40 between them. The release peg 48 with its smaller diameter portion for insertion into the bore 32 of the desoldering implement and the stopping shoulder 52 are clearly shown in FIG. 5.

Also illustrated in FIGS. 5 and 6 is the magazine for holding the spare tips 30. Within the open bottom of the body 38 of the tool 34 is disposed a pair of juxtaposed retaining shelves 90, 92 having a thickness slightly less than the axial length of the second, outer annular groove 68 in the tips 30. The shelves are relieved appropriately and are sufficiently pliable for the insertion and retention therebetween of the spare tips. Their removal from the magazine is described in connection with the discussion of FIG. 13 below.

In FIGS. 7 and 8 the forced removal of the nozzle 30 from its retaining bore 32 in the end cap portion 26 is illustrated. In FIG. 7 the desoldering implement is shown ready for insertion of its fixed tip 30 into the bore 42 of the flexible jaws 36, 37. During insertion, the tapered portion 70 of the tip 30 will spread the jaws until the gripping tabs 44, 46 snap into the outer annular groove 68 as shown in FIG. 8. At this point the end 28 of the end cap 20 is in contact with the cams 47, 49 at the outer ends of the jaws 36, 37.

To remove the tip 30 from its locked engagement in the end cap, the operator holds the tool 34 from rotation and squeezes the jaws 36, 37 together as indicated by the force arrows 94 while the body of the desoldering implement 10 is rotated about its axis as indicated by the arrow 96. When the ends 28 of the levering fins 22, 24 are rotated into contact with the cams 47, 49, the desoldering implement is driven away as indicated by the arrow 98 from the removal tool 34 while the latter retains the tip 30. Thusly, with the mechanical advantage of the inclined slope of the cam surfaces, the grip of the shoulder 54 in the inner, first groove 56 is broken and the tip, held now by the gripping tabs 46, 47 of the jaws 36, 37, is easily withdrawn from the end cap of the desoldering tool.

Once thusly removed from the end cap 20, however, the nozzle 30 continues to be firmly held by the gripping tabs 44, 46 of the jaws 36, 37 as shown in FIGS. 9 and 10.

With reference to FIGS. 11 and 12 the operation of the release peg 48 is illustrated. The end cap 20 of the desoldering tool 10 is placed over the peg 48 until its shoulder 52 abuts the end 28 of the end cap. As this insertion of peg 48 into the bore 32 of the end cap is accomplished, one of the levering fins 22, 24 is driven into the gap 40 between the jaws 36, 37. The cams 47, 49 cooperate with the end 28 of a fin to funnel the fin into the gap as shown. Thusly forcing the fin into the gap spreads the jaws 36, 37 whereby the gripping tabs 44, 46 release their hold within the annular groove 68 and the nozzle drops down through the bore 42 and out of the bottom of the removal tool 34. If more spreading of the jaws is desirable for this release function, the body of the desoldering tool 10 may be rotated as shown by the arrows 100 to cause the fin to force one of the jaws further away from the other. The tools 10, 34 may then be separated and the dropped out tip 30 discarded or returned to the magazine as a spare.

At the end of the steps in the previous figures, the end cap 20 of the desoldering tool 10 is empty regarding its desoldering tip. To install a replacement tip therein, the removal tool 34 is inverted, as shown in FIG. 13, to expose and make accessible the magazine of spare tips. As indicated, the end cap 20 is placed down over the taper 60 of the desired tip in the direction of the arrow 102 with sufficient force to lockingly engage the retaining shoulder 54 into the annular groove 56 of the tip. The desoldering tool 10 may then be withdrawn oppositely to the arrow 102 and the grip of the pliable shelf 90 in the other annular groove 68 of the tip will readily be released. The desoldering tool 10 is then ready again for use.

There have thus been disclosed and described the salient features of a presently preferred embodiment of the combination of the invention which achieve the objects and exhibit the advantages set forth hereinabove.

We claim:
1. A desoldering system comprising:
   A. a desoldering implement of the character having a molded plastic body having an elongated cylindri- cal barrel housing a spring actuated vacuum producing piston and having molded therewith a front end cap including a forwardly protruding cylindrical nose portion formed with a central, axially aligned nozzle retaining bore therethrough of a predetermined first diameter, said nose portion having an annular retaining shoulder formed in said bore and extending radially inwardly from said first diameter to a lesser second diameter and being axially spaced rearwardly of the front end of said nose portion, said nose portion also including at least one levering fin extending radially outwardly from the outer diameter of said nose portion and extending rearwardly from the front end of said nose portion along at least a portion of the length thereof;

B. a replaceable plastic nozzle of the character to be carried by said nose portion and extend forwardly therefrom for solder removing contact with a workpiece, said nozzle being tubular with an outer diameter in its central portion approximately equal to said first diameter and having an annular retention groove formed near its rear end, the inner diameter of the groove being approximately equal to said second diameter, and the axial lengths of said groove and said retaining shoulder being approximately equal, the outer diameter of the nozzle being tapered inwardly from a point just rearwardly of said groove to a reduced diameter, approximately equal to or less than said second diameter, at the rear of said nozzle, said nozzle further including a second annular groove formed about the circumference thereof at a point axially contiguous to and forwardly of said front end of said nose portion when said retaining shoulder and first annular groove are retentively engaged; and C. a nozzle removal tool having
 1. a hollow molded plastic body,
 2. a pair of flexible juxtaposed jaws carried by said body and extending away therefrom along a predetermined axis, said jaws being internally relieved to receive between them along said axis the forward portion of said replaceable nozzle, said jaws further each including an inwardly protruding gripping tab near its end and being of the character to grip said nozzle by being inserted into said second annular groove when the nozzle is received between said jaws, said jaws further having cam surfaces forming their outer ends and diverging away from said axis in a manner such that when said nozzle installed in said nose portion is received between said jaws and gripped by said gripping tabs, the front end of said levering fin engages a said cam surface and is forced away from said body of said removal tool when it is rotated, about said axis, with respect to said body, and
 3. release means carried by said body for guiding said levering fin between said jaws to separate them and cause the release thereby of said nozzle.

2. A hand held, spring actuated vacuum stroke desoldering implement comprising:
A. an elongated molded plastic cylindrical barrel;
B. a front end cap molded integrally therewith and formed with a forwardly extending nose portion having
 1. a nozzle retaining central bore extending axially therethrough of a predetermined inner diameter,
 2. a reduced diameter nozzle retaining annular shoulder disposed along said bore axially spaced from its front end, and
 3. at least one vane-like levering fin molded with said nose portion protruding radially outwardly therefrom and extending axially from its front end along at least a major portion of its axial length.

3. A replaceable plastic nozzle for a desoldering implement and comprising a tubular elongated body having a molten solder and air flow bore formed axially centrally therethrough and having:
A. a central body portion of a first predetermined diameter,
B. a first annular retaining groove formed at the rear of said central portion and having a reduced, second predetermined diameter,
C. a second annular, gripping groove formed at the front of said central portion,
D. a rear body portion the external surface of which is tapered from said first diameter at said first groove to a reduced diameter equal to or less than said second diameter at the rear end of said rear body portion, and
E. a forward tip portion extending forwardly from said second groove and having an outer diameter tapering from said first diameter to a reduced diameter at its front tip end.

4. A molded plastic removal tool for gripping and forcefully removing or replacing desoldering tool nozzles from or into, respectively, the nose portion of a hand held vacuum stroke desoldering implement, the tool comprising:
A. a hollow body portion;
B. a pair of juxtaposed flexible gripping jaws carried by said body portion and extending in a cantilevered manner upwardly therefrom along a predetermined nozzle axis, the jaws being mutually relieved to form between them an open ended cylinder-like chamber concentric with said axis for receiving one of said nozzles,
C. a gripping tab formed near the upper end of each of said jaws and protruding toward each other into said chamber to grip positively one of said nozzles when it is disposed in said chamber and said flexible jaws are urged toward each other,
D. symmetric cam surfaces forming the upper portions of said jaws and axially disposed between said gripping tabs and the upper, tips ends of said jaws, the cam surface of each jaw being substantially planar and inclined upwardly divergingly away from said nozzle axis.

5. The invention as set forth in claim 4 which further includes a release peg carried by said body portion and extending upwardly therefrom substantially parallel to said axis and equally contiguous to each of said jaws.

6. The invention as set forth in claim 5 in which said hollow body includes a magazine means for storing at least one spare said desoldering nozzle and comprising a pair of opposed pliable shelf and shelf edge means for readily releasably gripping and retaining said nozzle.

* * * * *